United States Patent [19]

Perdelwitz, Jr. et al.

[11] Patent Number: 5,968,855
[45] Date of Patent: Oct. 19, 1999

[54] NONWOVEN FABRICS HAVING LIQUID TRANSPORT PROPERTIES AND PROCESSES FOR MANUFACTURING THE SAME

[75] Inventors: Lee Edward Perdelwitz, Jr., Simpsonville; Guy Stanley Zimmerman, Jr., Greenville, both of S.C.

[73] Assignee: BBA Nonwovens Simpsonville, Inc., Simpsonville, S.C.

[21] Appl. No.: 08/810,595

[22] Filed: Mar. 4, 1997

[51] Int. Cl.$^6$ .......................................................... B32B 7/02
[52] U.S. Cl. ......................... 442/341; 442/347; 442/350; 442/351; 428/220; 38/144; 264/103
[58] Field of Search ...................................... 442/341, 347, 442/350, 351; 428/220; 38/144; 264/103

[56] References Cited

U.S. PATENT DOCUMENTS

| | | |
|---|---|---|
| 4,039,711 | 8/1977 | Newman . |
| 4,211,227 | 7/1980 | Anderson et al. . |
| 4,451,314 | 5/1984 | Knoke et al. . |
| 4,555,430 | 11/1985 | Mays . |
| 4,749,423 | 6/1988 | Vaalburg et al. . |
| 4,770,925 | 9/1988 | Uchikawa et al. . |
| 4,798,603 | 1/1989 | Meyer et al. . |
| 4,830,904 | 5/1989 | Gessner et al. . |
| 4,883,707 | 11/1989 | Newkirk . |
| 5,057,357 | 10/1991 | Winebarger . |
| 5,143,779 | 9/1992 | Newkirk et al. . |
| 5,318,552 | 6/1994 | Shiba et al. . |
| 5,368,925 | 11/1994 | Hosokawa et al. . |
| 5,418,045 | 5/1995 | Pike et al. . |
| 5,424,115 | 6/1995 | Stokes . |
| 5,443,893 | 8/1995 | Herzberg . |
| 5,460,884 | 10/1995 | Kobylivker et al. . |
| 5,470,640 | 11/1995 | Modrak . |
| 5,486,166 | 1/1996 | Bishop et al. . |
| 5,487,943 | 1/1996 | Kozulla . |
| 5,490,846 | 2/1996 | Ellis et al. . |
| 5,491,016 | 2/1996 | Kaiser et al. . |
| 5,500,281 | 3/1996 | Srinivasan et al. . |
| 5,522,810 | 6/1996 | Allen, Jr. et al. . |
| 5,532,050 | 7/1996 | Brooks . |
| 5,534,339 | 7/1996 | Stokes . |
| 5,534,340 | 7/1996 | Gupta et al. . |

*Primary Examiner*—Christopher Raimund
*Attorney, Agent, or Firm*—Alston & Bird LLP

[57] ABSTRACT

A nonwoven fabric which is particularly useful as a liquid transport layer in an absorbent product. The fabric is formed of a mixture of fibers of varying sizes and polymer compositions, selected to provide the desired liquid transport properties to the fabric, and thermally bonded by calendering to form a coherent fabric structure.

33 Claims, 1 Drawing Sheet

NONWOVEN FABRICS HAVING LIQUID TRANSPORT PROPERTIES AND PROCESSES FOR MANUFACTURING THE SAME

FIELD OF THE INVENTION

The present invention relates to nonwoven fabrics and to processes for producing the nonwoven fabrics. More specifically, the invention relates to nonwoven fabrics suitable for use in absorbent products, such as disposable diapers, adult incontinence pads and sanitary napkins, and the like.

BACKGROUND OF THE INVENTION

Disposable absorbent products, such as disposable diapers, sanitary napkins, and the like, typically include a liquid impermeable outer covering, an absorbent layer, and an inner layer which contacts the skin of the wearer. The inner layer is referred to in the art as coverstock, topsheet, or, in diaper applications, diaper liners.

Typically, the liner or coverstock layer is a liquid permeable, porous nonwoven fabric, such as a carded web or a spunbonded web. The absorbent core can include wood pulp fibers and optionally superabsorbent particles designed to absorb many times their own weight in liquid. To provide a comfortable yet effective product, the liner layer ideally permits liquid to flow through it rapidly into the absorbent layer ("rapid strike through") but does not permit or, at a minimum does not facilitate, re-transmission of liquid from the absorbent layer to the "wearer" side of said inner layer ("resists rewet").

Many conventional absorbent products, however, do not provide adequate liquid strike through and rewet properties. Often liquid is delivered to the absorbent system at a rate faster than the rate at which the system can transport the liquid away from the wearer's skin into the absorbent core (i.e., the liquid uptake rate of the system is slower than the liquid delivery rate). Even if the absorbent system can adequately handle an initial liquid surge, once wetted, the absorbent material can lose resiliency and collapse, thus affecting the ability of the system to handle subsequent liquid surges. As a result, at least a portion of the liquid can pool on the liner layer and/or wick back to the liner layer adjacent the wearer's skin. This can cause wearer discomfort, skin irritation, and leakage.

Design features, such as elastic gathers at the leg and waist region of the product, can alleviate leakage. Alterations to the design and/or amount of the absorbent material can also reduce these problems. While these and other design modifications can minimize leakage, they do not alleviate these problems, and can in some cases aggravate the problem.

Additional layers ("surge" layers) can be introduced between the absorbent layer and the liner layer to improve fluid uptake and to reduce wetback. Typically, surge layers are relatively thick, high loft carded nonwoven webs bonded using through-air bonding techniques. Through-air bonding bonds the fibers of the fabric together to provide fabric integrity while also maintaining the desired fabric structure (such as loft, density, etc.) to provide the desired liquid transport properties. Exemplary through-air bonded nonwoven webs useful as surge layers in absorbent personal care products are described in U.S. Pat. No. 5,486,166 to Bishop et al., U.S. Pat. No. 5,490,846 to Ellis et al., and U.S. Pat. No. 5,522,810 to Allen, Jr. et al. These patents recognize that through-air bonding should be used to control the structure of the fabric (such as level of compression or collapse of the structure).

While these and other fabrics can be effective, it can be difficult to provide through-air bonded fabrics which have adequate liquid transport properties yet also have desired strength, bulkiness, compressibility, resilience, and the like. Further, manufacturing through-air bonded carded fabrics can be slow, and the fabrics can be expensive relative to other types of nonwoven fabrics. Still further, these fabrics are typically provided as roll goods with small fabric yardages per roll, thus increasing shipping costs.

Chemically bonded (i.e., adhesively bonded) carded nonwoven fabrics and calendered carded nonwoven fabrics also can be used as a liquid transport layer in an absorbent product. These fabrics, however, have relatively low loft, and thus the liquid transport properties are not as desirable as those exhibited by through-air bonded carded webs.

SUMMARY OF THE INVENTION

The present invention provides calendered nonwoven fabrics having loft, density and/or pore size advantageous for imparting liquid transport properties to the fabric. The nonwoven fabrics of the invention can exhibit superior liquid transport properties, i.e., permit liquid to flow through the fabric rapidly while retarding re-transmission of the liquid to the surface of the fabrics. These properties can be achieved at reasonable cost and with minimal adverse impact on other desirable properties, such as size (bulkiness or thickness), strength, and the like. The fabrics are particularly useful as liquid acquisition/distribution or liquid transport components in disposable absorbent products such as diapers and the like.

The nonwoven fabrics of the invention are calender bonded fabrics formed of a mixture of fibers of varying sizes (or denier) and polymer compositions. The fabrics include fibers formed of a relatively high melt thermoplastic polymer and fibers formed of a relatively low melt thermoplastic polymer. The fabric is thermally treated by calendering so that the low melt fibers soften and bind the fibers together to provide integrity to the fabric. However, the higher melting staple fibers advantageously maintain their discrete individual fiber integrity, crimp, and loft, thereby imparting desirable loft, density, and pore size of the resultant calendered fabric.

The denier of the low melt fibers and the high melt fibers is also selected to provide the desired fabric properties after thermal treatment by calendering. Preferably, the high melt fibers have an average denier which is greater than the average denier of the low melt fibers, which can also result in the desired fabric density, pore size, and other properties.

Calendered nonwoven fabrics are well known in the art, but conventionally are not used as liquid transport components of disposable absorbent products because of their low loft, small pore size, undesirable liquid acquisition and rewet properties, and the like. In contrast to conventional calendered fabrics, the fabrics of the invention have high loft, low density, large pore size, and thus desirable liquid transport properties, as result of the selection of fiber denier and polymer composition.

The calendered fabrics of the invention can be produced more economically than conventional through-air bonded fabrics, due in part to inherent processing limitations associated with through-air bonding, such as relatively slow throughput rates. Further, the fabrics of the invention can provide economies in shipment, because more yardage of the fabric can be supplied per roll as compared to through-air bonded fabrics. Yet despite the use of calendering to thermally bond the fabrics of the invention, the fabrics exhibit desirable loft and liquid transport properties, in contrast to conventional calendered fabrics, which can have relatively low loft, and thus undesirable liquid transport properties.

Another aspect of the invention is a disposable absorbent article which includes a calendered fabric of the invention as a component thereof. In this embodiment of the invention, an absorbent body or layer is sandwiched between a liquid permeable liner layer and a substantially liquid impermeable backsheet layer. The fabric of the invention is secured between the absorbent core and the liner layer, and acts to rapidly transport fluid from the liner layer adjacent a wearer's skin and into the absorbent core without substantial re-wet or retransmission of the fluid back to the wearer's skin.

BRIEF DESCRIPTION OF THE DRAWINGS

In the drawings which form a portion of the original disclosure of the invention.

DETAILED DESCRIPTION OF THE INVENTION

The present invention will now be described more fully hereinafter with reference to the accompanying drawings, in which an exemplary embodiment of the invention is shown. This invention may, however, be embodied in many different forms and should not be construed as limited to the embodiment set forth herein. Rather, this embodiment is provided so that the disclosure will be thorough and complete, and will fully convey the scope of the invention to those skilled in the art. Like numbers refer to like elements throughout. For purposes of clarity the scale has been exaggerated.

The nonwoven fabrics of the invention may be used as a component in a variety of products. The fabrics of the invention are particularly useful as liquid transport components in disposable absorbent personal care products, such as diapers, incontinence pads, training pants, sanitary napkins, and the like; in wipes; in bandages; and the like.

Figure 1:
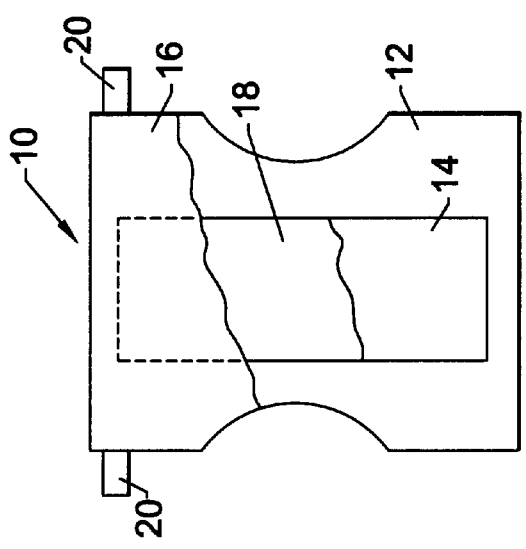
FIG. 1 is a fragmentary top plan view of an absorbent article incorporating a nonwoven fabric in accordance with the invention.

FIG. 1 illustrates a fragmentary top plan view of a disposable diaper, designated generally at 10. Disposable diaper 10 includes a substantially liquid impermeable backsheet layer 12, an absorbent layer 14 positioned on backsheet layer 12, and a liquid permeable topsheet layer 16 positioned on absorbent layer 14. Diaper 10 also includes a calendered nonwoven fabric 18 in accordance with the present invention disposed between absorbent layer 14 and topsheet layer 16.

Liquid transport layer 18 is a nonwoven fabric which includes a mixture of fibers of varying sizes and polymer compositions thermally bonded by calendering. Fiber sizes and polymer compositions are selected to provide both fabric coherency and liquid transport properties, as described below.

The fabrics of the invention generally include a mixture of fibers formed of a relatively high melt thermoplastic polymer and fibers formed of a relatively low melt thermoplastic polymer. The mixture of fibers may also include other, non-thermoplastic fibers, such as cotton fibers, wool fibers, wood pulp fibers and the like. The polymer compositions of the low melt fibers and the high melt fibers are selected so that the resultant fabric exhibits fabric integrity upon thermal treatment with minimal adverse impact on the desired fabric properties, such as loft, density, and the like.

Specifically, when the fabric is thermally treated by calendering, the low melt fibers can soften and fuse to one another and to the high melt fibers and thus act as binder fibers to bind the fibers together to provide integrity to the fabric. The high melt fibers advantageously do not substantially soften and lose their individual discrete fibrous nature when the web is calendered so that the high melt fibers contribute the desired loft, density, pore size, and the like to the fabrics of the invention. The polymer compositions of the low melt and high melt fibers are preferably selected so that the difference between the relative melting points of the low melt and high melt fibers of the fabric is at least about 10° C.

Exemplary thermoplastic polymers useful for forming the thermoplastic fibers include, but are not limited to, polyolefins such as polypropylene and polyethylenes, polyesters such as poly(ethylene terephthalate), polyamides such as poly(hexamethylene adipamide) and poly(caproamide), and blends and copolymers thereof. The thermoplastic fibers can also be bicomponent or multicomponent fibers, such as sheath/core, side-by-side, sectorized or similar bicomponent fibers wherein at least one component of the fiber is a low melting material. Exemplary bicomponent fibers include polyolefin/polyolefin sheath/core fibers such as a polyethylene/polypropylene sheath/core fibers and polyolefin/polyester sheath/core fibers, such as a polyethylene/polyethylene terephthalate sheath/core fiber. The fibers can also be crimped fibers. In one embodiment of the invention, the low melt fibers are polyolefin staple fibers and the high melt fibers are polyester or polyamide staple fibers.

The mixture of fibers also include low melt fibers and high melt fibers of different sizes or denier. The difference between denier of the low melt fibers and the high melt fibers is also selected to provide the desired fabric properties after thermal treatment by calendering, for example, suitable loft, density, pore size and the like for a particular end use application. Generally, desirable fabric properties can be achieved using high melt fibers having an average denier which is greater than the average denier of the low melt fibers, although the converse can also apply. Exemplary average fiber denier range from about 1.5 to about 15, preferably about 15, for the high melt fibers, and from about 1.5 to about 15, preferably about 6, for the low melt fibers, although fibers sizes outside of these ranges are also contemplated for use in accordance with the present invention.

The low melt fibers are present in the fabrics of the invention in an amount sufficient to secure the fibers of the web together to form a coherent unitary fabric. The content of the low melt fiber can be adjusted to provide coherency to the overall combined web without adding an undesirably stiff or boardy feeling to the web, or without significantly adversely impacting liquid transport properties. The specific content of the low melt fiber will be dependent, at least to some extent, on the type of low melt fiber used and on the type of high melt fiber used. A preferred mixture of fibers includes about 10 to about 90 weight percent, more preferably about 30 to about 70 weight percent, of fibers formed of a low melt polymer composition, and about 90 to about 10 weight percent, more preferably about 70 to about 30 weight percent, fibers formed of a high melt polymer composition.

The nonwoven fabric of the invention is preferably formed of a mixture of staple fibers, and the fabric may be formed by any of the methods known in the art for forming a nonwoven web of staple fibers, such as carding, air laying, garnetting, and similar processes known in the art. Although the use of staple fibers is currently preferred, the nonwoven webs of the invention can also be formed of mixtures of continuous filaments of different polymer compositions and denier. Continuous filament webs can be formed, for example, by spunbonding processes as known to the skilled artisan. Spunbonding processes generally include the following steps: (1) extruding continuous filaments; (2) quenching the filaments; (3) drawing or attenuating the filaments by a high velocity fluid; and (4) collecting the filaments on a surface to form a web. Exemplary spunbonding techniques are described in U.S. Pat. Nos. 3,338,992; 3,341,394; 3,276,944; 3,502,538; 3,502,763; 3,509,009; 3,542,615; and 3,692,618.

Returning now to FIG. 1, as illustrated, backsheet layer 12 and topsheet layer 16 are essentially coextensive and extend out past the edges of absorbent layer 14 and liquid transport layer 18 to form marginal edges about the periphery of diaper 10. Diaper 10 is illustrated as having a general hourglass or I-shape, but as will be appreciated by the skilled artisan, other product shapes may be used, depending upon the desired properties and end use of the product. Diaper 10 can also include fasteners 20 for fastening the diaper on the wearer. As illustrated, fasteners 20 are adhesive tape tabs; however, any of the fasteners known in the art, such as hooks, clips, snaps, hook and loop types fastener systems such as Velcro and the like, may be used.

Backsheet layer 12 may be any of the types of substantially liquid impermeable layers known in the art for use with disposable absorbent products, including but not limited to plastic films, fibrous nonwoven webs, foams and combinations of these and other suitable materials. For example, backsheet layer 12 can be a polyolefin film, can include a nonwoven material, such as a spunbonded nonwoven web, which has been suitably treated to impart a desired degree of liquid impermeability thereto, for example, by combining the nonwoven material with a polymer film, and the like as known in the art. To increase wearer comfort, backsheet layer 12 can also be breathable, either due to the nature of the backsheet component or by treating the backsheet material. For example, the breathability of plastic films can be increased by aperturing and/or through use of microporous films which often include fillers, as known in the art. Such filler containing films can be stretched or crushed to create pores adjacent the filler to provide a path through the film which will permit for example water vapor to be transmitted therethrough. Other films are available which transmit water vapor using diffusion mechanisms.

Absorbent layer 14 is used to absorb body fluids or other liquids delivered to it through topsheet 16 and liquid transport layer 18. The absorbent layer 14 can be made from a wide variety of materials known in the art including, but not limited to, natural and synthetic wood pulp fluff fibers, hydrophilic thermoplastic fibers and/or thermoplastic fibers which may have been treated to impart hydrophilic characteristics thereto, and combinations thereof. For example, absorbent layer 14 can be a preformed web substantially made of cotton-like woody pulp. Wood pulp may be included in the absorbent layer, preferably by incorporating the wood fiber from a hammer milled water laid web or from an air laid web which may contain staple textile fibers, such as cotton, reconstituted cellulose fibers, e.g., rayon and cellulose acetate, polyolefins, polyamides, polyesters, and acrylics. The absorbent layer may also include an effective amount of an inorganic or organic high-absorbency (e.g., superabsorbency) material as known in the art to enhance the absorptive capability of the absorbent layer.

Topsheet or liner layer 16 is designed to contact the wearer's skin and accordingly advantageously is soft to the touch yet abrasion resistant. The topsheet is also preferably liquid permeable, thus allowing liquid to pass therethrough into the absorbent layer 14. Suitable materials for topsheet 16 include, but are not limited to, carded webs, continuous filament webs such as spunbonded webs, and the like, as well as liquid pervious films, and laminates of films and nonwoven fabrics.

The liquid transport fabric of the invention can be positioned between the liner or topsheet layer and the absorbent layer, as illustrated in FIG. 1. Alternatively, the fabric of the invention can be used as the liner or topsheet component of the product, or it can form a portion of the liner or absorbent core in the form of a composite which may or may not be laminated, for example, thermally, adhesively, hydroentangling, needling, stitching or other bonding techniques as known in the art.

Liquid transport layer 18 can have the same general shape and width and length dimensions of absorbent layer 14 or can be made to be smaller or larger than absorbent layer 14. Liquid transport layer 18 also can be made to the same general shape and/or width and/or length dimensions as the liquid permeable topsheet layer 16 and/or liquid impermeable backsheet layer 12.

The nonwoven fabric may be combined with backsheet layer 12, absorbent layer 14 and topsheet layer 16, and any other components of the article, in any of the ways known in the art, such as gluing with lines of hot-melt adhesive, seaming with ultrasonic welding, thermal bonding, high pressure bonding and the like.

The calendered nonwoven fabric of the present invention advantageously permits liquid to rapidly flow through it into the absorbent layer but does not facilitate re-transmission of liquid back from the absorbent layer to the body side of the topsheet. Although not wishing to be bound by any explanation of the invention, it is believed that the liquid transport fabric of the invention acts as a space distancing topsheet 16 from absorbent layer 14 to reduce or minimize liquid flow back from the absorbent core to the wearer side of the article. The liquid transport fabric of the invention also can act as a "fluid reservoir" to temporarily hold and then distribute fluids. These features can advantageously prevent rewet and/or liquid pooling on a surface of the topsheet adjacent the wearer's skin, resulting from disparities in liquid surge rates and liquid absorption rates, reduced liquid uptake resulting from multiple liquid surges into a wetted absorbent structure, and/or inadequate liquid distribution within the absorbent core to more remote portions thereof.

Further, the fabrics of the invention can be compression resistant and can maintain the desired spatial relationship between absorbent layer 14 and liner layer 16 even under compressive forces (for example, resulting when the wearer sits). The fabrics can also be resilient, "springing" back to substantially its original construction after compressive forces are released. This can be advantageous because fabric pore size, thickness, density, and the like are not significantly adversely impacted by compression forces or loads.

The fabrics of the invention can also have sufficient strength to allow for converting it, i.e., incorporating it into the final product, and for resistance to failure during vigorous movements by the user.

The fabrics of the invention typically have a basis weight of about 10 to 100 grams per square meter, preferably about 20 to 50 grams per square meter. Fabric thickness (or caliper) can vary, depending upon the specific end use of the fabric and desired properties, including basis weight, and can range from about 20 to about 50 mils. The fabrics also preferably have a density (uncompressed) of about 0.02 to about 0.06 grams per cubic centimeter, more preferably an uncompressed density of about 0.035 to about 0.045 grams per cubic centimeter. Pore size of the fabrics of the invention can also vary. Generally, when separate topsheet and liquid transport layers are provided in a diaper or other disposable absorbent product, the average pore size of the fabric of the invention is larger than the average pore size of the topsheet layer. Advantageously, the pore size of the fabric of the invention ranges from about 50 to about 300 microns (uncompressed), and more preferably from about 100 to about 250 microns. Under a load of about 0.04 psi, fabric density advantageously ranges from about 0.035 to about 0.045 grams per cubic centimeter and pore size can range from about 150 to about 225 microns. Fabric thickness can be determined using ASTM D1777 test method. Pore size can be determined using the techniques described in S. L. Samuels, International Nonwovens Journal, vol. 6, no. 4, pps. 49–52 (1995).

Figure 2:
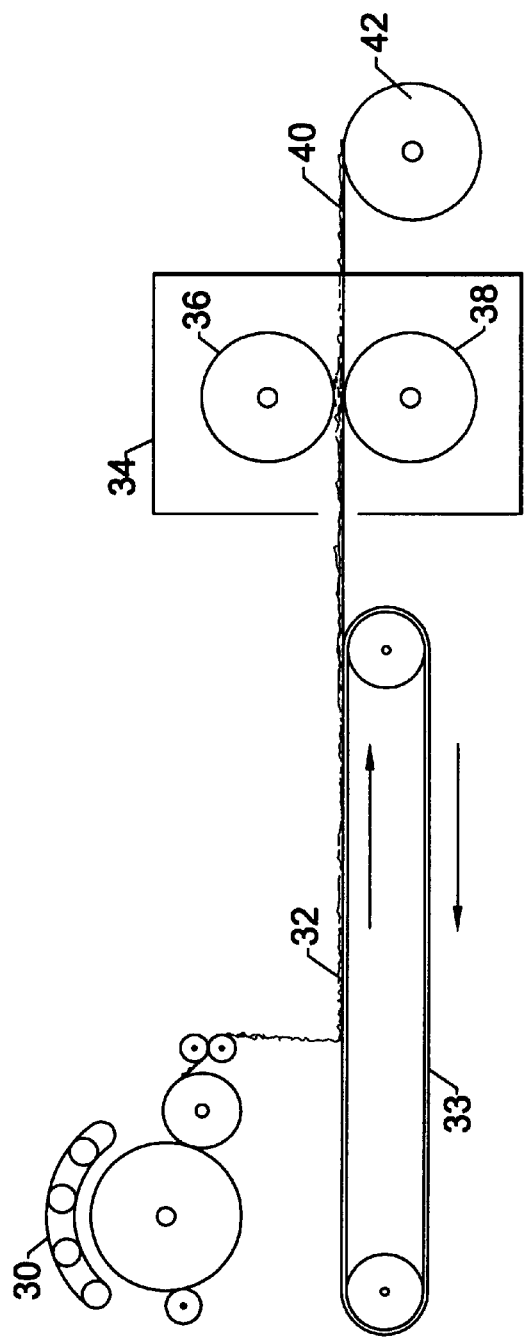
FIG. 2 is a schematic illustration of one process for producing a calendered nonwoven fabric in accordance with the invention.

FIG. 2 schematically illustrates a preferred process and apparatus for forming the nonwoven fabrics of the invention. A conventional carding apparatus 30 forms a carded web 32 onto forming screen 33. The carded wed 32 includes a mixture of staple fibers of different polymer compositions and denier as described above. Carding processes are well known in the art, and generally include the steps separating clumps of staple fibers into individual fibers and forming the staple fibers into a coherent web.

The carded web 32 is conveyed in the longitudinal direction as indicated in FIG. 2 to a thermal treatment station 34, illustrated in FIG. 2 as heated calender rolls 36 and 38. Here the web 32 is treated to form a plurality of thermal bonds which secure the staple fibers together to form the product of the invention, fabric 40. Specifically, the web 32 is thermally treated by calendering so that the low melt fibers soften and become tacky, and fuse together contacting portions of the low melt fibers and the high melt fibers to form a coherent nonwoven fabric of the invention 40. Preferably, the high melt fibers do not exhibit significant loss of individual fiber structural integrity.

Bonding conditions, including roll temperature and pressure, vary according to the particular polymer compositions used and are known in the art for differing polymers. For example, to bond a web formed of a mixture of low melt polypropylene fibers and high melt polyester fibers, the roll pressure and temperature can range from about 246 to about 434 pli and from about 145° C. to about 165° C., respectively.

The heated calender rolls 36 and 38 in FIG. 2 may consist of a pair of pattern rolls, a pattern roll and a smooth steel roll, a pattern roll and a rubber roll or other roll combinations known in the art. The pattern of the calender rolls may be any of those known in the art, including spot bonding patterns, helical bonding patterns, line bonding patterns, and the like. The term spot bonding is used herein to be inclusive of continuous or discontinuous pattern bonding, uniform or random point bonding, or a combination thereof, all as are well known in the art.

The thermally bonded calendered nonwoven fabric 40 is then removed from the thermal treatment station 34 and wound by conventional means onto roll 42. The nonwoven fabric can be stored on roll 42 or immediately passed to end use manufacturing processes, for example, for use in bandages, diapers, disposable undergarments, personal hygiene products, and the like.

The resultant thermally bonded fabric can have hydrophilic properties, for example, by incorporating hydrophilic fibers therein, by treating the fabric to impart hydrophilic properties thereto, and the like. For example, when the fabric is formed of a hydrophobic material, such as polypropylene, hydrophilic properties can be imparted by adding an additive to the polymer which upon extrusion or upon post formation treatment migrates to the surface of the fibers to impart hydrophilic properties to the surface of the fibers. Alternatively, the fabric can be treated with any of the surfactants known in the art to thereby impart hydrophilic properties to the fabric. U.S. Pat. No. 5,104,728 to Obermeyer and Cashin, the entire disclosure of which is hereby incorporated by reference, describes one such surfactant treatment.

The following examples serve to illustrate the invention but are not intended to be limitations thereon.

EXAMPLE 1

Carded webs of the invention having a basis weight of approximately 20 and 40 gsm are formed of a mixture of about 50 weight percent 6 denier per filament (dpf) polypropylene staple fibers commercially available from Hercules under the trade name T196 and about 50 weight percent 15 dpf polyester staple fiber commercially available from DuPont under the trade name Type 11A. The carded webs are directed through cooperating calender rolls at a speed of about 96 meters per minute. The rolls surface temperature is 155° C. and the rolls are adjusted to a pressure of about 340 pounds per linear inch (phi).

Caliper, density, basis weight, and average pore size of the samples are evaluated, using the test methods described above. The results are set forth in Table 1 below. These properties are also measured for the comparative fabrics as noted in Table 1.

TABLE 1

| Fabric | Basis weight (gsm) | Denier (dpf) | Caliper (mils) | Density (g/cc) | Approx. pore size (μm) |
|---|---|---|---|---|---|
| Carded thermobond | 20 | 6.0 PP 15.0 PET | 20 | 0.04 | 177 |
| Carded thermobond | 40 | 6.0 PP 15.0 PET | 40 | 0.04 | 200 |
| Topsheet | 20 | 2.0 | 10.5 | 0.076 | .59 |
| Thru-air bond | 58 | 2.8 PE 6.4 PET | 62 | 0.037 | 155 |
| Carded chembond | 27 | 5.8 PET | 11.1 | 0.096 | 92 |

Note: Carded thermobond refers to the fabrics of the invention. Thru-air bond refers to a thru-air bonded fabric commercially available from Kimberly Clark. PP is polypropylene and PET is polyester.

EXAMPLE 2

The fabrics described above in Example 1, including the fabrics of the invention and the comparative fabrics, are evaluated as liquid transport layers in a diaper as follows. The side and leg cuff elastic components are removed from an Ultratrim Baby Steps 4 for Him diaper available from Kimberly Clark. The leg cuffs are retained, and the diaper is laid out flat. Other diaper types can be used in this test, but the same diaper type should be used consistently.

A synthetic urine solution is prepared of a 0.5% saline solution, dyed red with 15 drops of red food coloring per 1000 mL solution. NaCl is reagent grade from Mallinckrodt, and food coloring is McCormick brand red food coloring.

The nonwoven highloft cover (or topsheet) and tissue layers of the diaper are removed, exposing the core and keeping the leg cuffs in place. A 4.25" wide by 16" long fabric (of the invention or comparative fabrics) is placed over the core with the leading edge at the bottom edge of the front waistband. This fabric layer is covered with a topsheet layer (available from Fiberweb North America as FPN 308 carded thermal bonded polypropylene, cut into 5" by 16" size).

The liquid acquisition properties are tested using a test apparatus comprising 4" wide by 12" long by ½₁" thick clear plexiglass plate. The plate has a 2" i.d. hole cut 6" o.c. from the leading edge of the plate. Extending perpendicular from the hole is a 2" i.d. plexiglass tube 6" high functioning as a reservoir. The apparatus imparts 0.03 psi loading.

To test the sample diaper, the acquisition rate apparatus orifice is centered 61" from the leading bottom edge of the front waistband of the diaper and centered within the leg cuffs. At 0 minutes, 100 mL of the synthetic urine solution is added into the tube and the time is recorded to empty the apparatus as "acquisition rate one" in seconds. At 10 minutes, after the original insult, 100 mL synthetic urine solution is added into the tube, and the time is recorded to empty the apparatus as "acquisition rate two" in seconds. At 20 minutes after the original insult, 100 mL of synthetic urine is added into the tube, and the time is recorded to empty the apparatus as "acquisition rate three" in seconds.

At 50 minutes after the original insult, the apparatus is removed, and two pre-weighed filter papers (5" squares, Eaton Dikeman No. 939) are centered over the insulted area. Immediately thereafter, 4" by 4" compression weight equivalent is applied to 0.5 psi loading. This is left in place for two minutes. After two minutes, the weight is removed and the filter paper is immediately reweighed. The difference in weight is recorded as "rewet two" in grams.

The results are set forth in Table 2 below. The result reflect average of three samples.

TABLE 2

| Fabric | Basis weight (gsm) | Strike-thru 1 (sec) | Strike-thru 2 (sec) | Strike-thru 3 (sec) | Rewet (grams) |
|---|---|---|---|---|---|
| Carded thermobond | 20 | 24.7 | 24.3 | 26.2 | 0.66 |
| Carded thermobond | 40 | 17.6 | 17.2 | 18 | 0.24 |
| Topsheet | 20 | 32.5 | 56.7 | 66.8 | 2.5 |
| Thru-air bond | 58 | 17.7 | 19.7 | 23.1 | 0.21 |
| Carded chembond | 27 | 28.7 | 34 | 35.5 | 1.41 |

The invention has been described in considerable detail with reference to its preferred embodiments. However, it will be apparent that numerous variations and modifications can be made without departure from the spirit and scope of the invention as described in the foregoing specification and defined in the appended claims.

That which is claimed is:

1. A calendered liquid transport nonwoven fabric comprising:

a mixture of low melt thermoplastic polymer fibers and high melt thermoplastic polymer fibers, said high melt fibers having an average denier which is different from the average denier of said low melt fibers; and a plurality of thermal bonds formed from the polymer of said low melt fibers and bonding said low melt fibers and said high melt fibers of said calendered fabric to one another to form a coherent web, said calendered fabric having a caliper of about 20 to about 50 mils, an uncompressed density of about 0.02 to about 0.06 grams per cubic centimeter, and an uncompressed pore size of about 50 to about 300 microns.

2. The fabric of claim 1, wherein at least a portion of said high melt fibers have a substantially discrete fibrous form.

3. The fabric of claim 1, wherein said fabric has a basis weight of about 20 to 50 grams per square meter, an uncompressed density of about 0.035 to about 0.045 grams per cubic centimeter, and an uncompressed pore size of about 100 to about 250 microns.

4. The fabric of claim 1, wherein said fabric has a basis weight of about 20 to 50 grams per square meter, a density of about 0.035 to about 0.045 grams per cubic centimeter, and a pore size of about 150 to about 225 microns, under compression of about 0.04 pounds per square inch (psi).

5. The fabric of claim 1, wherein the difference in melting point between said low melt fibers and said high melt fibers is at least about 10° C.

6. The fabric of claim 1, wherein said fabric is a carded fabric.

7. The fabric of claim 1, wherein said mixture of fibers comprises a mixture of low melt polyolefin staple fibers and high melt polyester or polyamide staple fibers.

8. The fabric of claim 7, wherein said low melt polyolefin staple fibers are selected from the group consisting of polypropylene staple fibers, polyethylene staple fibers, polyolefin copolymer staple fibers, polyolefin bicomponent staple fibers, polyolefin blend staple fibers, and mixtures thereof.

9. The fabric of claim 1, comprising about 10 to about 90 weight percent low melt fibers and about 90 to about 10 weight percent high melt fibers.

10. The fabric of claim 9, comprising about 30 to about 70 weight percent low melt fibers and about 70 to about 30 weight percent high melt fibers.

11. The fabric of claim 1, wherein said low melt fibers have an average denier which is less than the average denier of said high melt fibers.

12. The fabric of claim 11, wherein said low melt fibers have an average denier from about 1.5 to about 15 and said high melt fibers have an average denier from about 1.5 to about 15.

13. The fabric of claim 1, wherein said low melt fibers are polypropylene staple fibers having an average denier of about 6 and said high melt fibers are polyester staple fibers having an average denier of about 15.

14. An absorbent product comprising a liquid permeable topsheet, a liquid impermeable bottom sheet, and an absorbent core disposed therebetween, said product further comprising a liquid transport layer disposed between said absorbent core and said topsheet, said liquid transport layer comprising a calendered nonwoven fabric of comprising a mixture of low melt thermoplastic polymer fibers and high melt thermoplastic polymer fibers, said high melt fibers having an average denier which is different from the average denier of said low melt fibers, said calendered fabric having a caliper of about 20 to about 50 mils, an uncompressed density of about 0. 02 to about 0.06 grams per cubic centimeter, and an uncompressed pore size of about 50 to 300 microns; and a plurality of thermal bonds formed from the polymer of said low melt fibers and bonding said low melt fibers and said high melt fibers of said calendered fabric to one another to form a coherent web.

15. The product of claim 14, wherein said product is selected from the group consisting of diapers, training pants, incontinence devices, sanitary napkins, and bandages.

16. The product of claim 14, wherein at least a portion of said high melt fibers has a substantially discrete fibrous form.

17. The product of claim 14, wherein said fabric has a basis weight of about 20 to 50 grams per square meter, an uncompressed density of about 0.035 to about 0.045 grams per cubic centimeter, and an uncompressed pore size of about 100 to about 250 microns.

18. The product of claim 14, wherein said fabric has a basis weight of about 20 to 50 grams per square meter, a density of about 0.035 to about 0.045 grams per cubic centimeter, and a pore size of about 150 to about 225 microns, under compression of about 0.04 pounds per square inch (psi).

19. The product of claim 14, wherein the difference in melting point between said low melt fibers and said high melt fibers is at least about 10° C.

20. The product of claim 14, wherein said fabric is a carded fabric.

21. The product of claim 14, wherein said mixture of fibers comprises a mixture of low melt polyolefin staple fibers and high melt polyester or polyamide staple fibers.

22. The product of claim 21, wherein said low melt polyolefin staple fibers are selected from the group consisting of polypropylene staple fibers, polyethylene staple fibers, polyolefin copolymer staple fibers, polyolefin bicomponent staple fibers, polyolefin blend staple fibers, and mixtures thereof.

23. The product of claim 14, wherein said fabric comprises about 10 to about 90 weight percent low melt fibers and about 90 to about 10 weight percent high melt fibers.

24. The product of claim 23, wherein said fabric comprises about 30 to about 70 weight percent low melt fibers and about 70 to about 30 weight percent high melt fibers.

25. The product of claim 14, wherein said low melt fibers have an average denier which is less than the average denier of said high melt fibers.

26. A process for producing a calendered liquid transport nonwoven fabric, the process comprising thermally treating by calendering a nonwoven fabric comprising a mixture of low melt thermoplastic polymer fibers and high melt thermoplastic polymer fibers, said high melt fibers having an average denier which is different from the average denier of said low melt fibers, under conditions sufficient to form a plurality of thermal bonds formed from the polymer of said low melt fibers and bonding said low melt fibers and said high melt fibers of said calendered fabric to one another to form a coherent web, and further to form a fabric having a caliper of about 20 to about 50 mils, an uncompressed density of about 0.02 to about 0.06 grams per cubic centimeter and an uncompressed pore size of about 50 to about 300 microns.

27. The process of claim 26, wherein said calendering step is conducted under conditions sufficient to maintain the discrete fibrous identity of at least a portion of said high melt fibers.

28. The process of claim 26, further comprising prior to said thermal treatment step the step of forming a web of a mixture of said low melt fibers and said high melt fibers, and wherein said thermal treatment step comprising directing said web through cooperating thermal bonding rolls.

29. The process of claim 28, wherein said forming step comprises forming a carded web comprising a mixture of low melt polyolefin staple fibers and high melt polyester or polyamide staple fibers, said high melt staple fibers having an average denier greater than the average denier of said low melt staple fibers.

30. The process of claim 29, wherein said forming step comprises forming a carded web comprising about 10 to about 90 weight percent low melt polypropylene staple fibers having an average denier of about 1.5 to about 15 and about 90 to about 10 weight percent high melt polyester staple fibers having an average denier from about 1.5 to about 15.

31. A process for forming a personal care absorbent product, comprising securing together as a coherent product a liquid permeable top sheet and a bottom sheet with an absorbent core disposed therebetween, and a liquid transport layer disposed between said top sheet and said absorbent core, said liquid transport layer comprising a nonwoven fabric comprising a mixture of low melt thermoplastic polymer fibers and high melt thermoplastic polymer fibers, said high melt fibers having an average denier which is different from the average denier of said low melt fibers, and a plurality of thermal bonds formed from the polymer of said low melt fibers and bonding said low melt fibers and said high melt fibers of said calendered fabric to one another, said calendered fabric having a caliper of about 20 to 40 mils, an uncompressed density of about 0.02 to about 0.06 grams per centimeter and an uncompressed pore size of about 50 to about 300 microns.

32. A calendered liquid transport nonwoven fabric comprising:
    a mixture of low melt polypropylene staple fibers having an average denier of about 6 and high melt polyester staple fibers having an average denier of about 15; and
    a plurality of thermal bonds formed from the polymer of said low melt polypropylene staple fibers and bonding said low melt polypropylene staple fibers and said high melt polyester staple fibers of said calendered fabric to one another to form a coherent web, said calendered fabric having a caliper of about 20 to about 50 mils, an uncompressed density of about 0.02 to about 0.06 grams per cubic centimeter, and an uncompressed pore size of about 50 to about 300 microns.

33. An absorbent product comprising a liquid permeable top sheet, a liquid impermeable bottom sheet, and an absorbent core disposed therebetween, said product further comprising a liquid transport layer disposed between said absorbent core and said top sheet, said liquid transport layer comprising a calendered nonwoven fabric comprising a mixture of low melt polypropylene staple fibers having an average denier of about 6 and high melt polyester staple fibers having an average denier of about 15 and a plurality of thermal bonds formed from the polymer of said low melt polypropylene fibers and bonding said low melt polypropylene staple fibers and said high melt polyester staple fibers of said calender fabric to one another to form a coherent web, said calender fabric having a caliper of about 20 to about 50 mils, an uncompressed density of about 0.02 to about 0.06 grams per cubic centimeter, and an uncompressed pore size of about 50 to about 300 microns.

* * * * *